US009662437B2

(12) United States Patent
Moosai

(10) Patent No.: US 9,662,437 B2
(45) Date of Patent: May 30, 2017

(54) INFUSION PUMP PRESSURE PLATE

(71) Applicant: Smiths Medical ASD, Inc., Plymouth, MN (US)

(72) Inventor: Shiva Moosai, Plymouth, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 0 days.

(21) Appl. No.: 15/303,684

(22) PCT Filed: Apr. 23, 2015

(86) PCT No.: PCT/US2015/027307
§ 371 (c)(1),
(2) Date: Oct. 12, 2016

(87) PCT Pub. No.: WO2015/167927
PCT Pub. Date: Nov. 5, 2015

(65) Prior Publication Data
US 2017/0028126 A1 Feb. 2, 2017

Related U.S. Application Data

(60) Provisional application No. 61/985,110, filed on Apr. 28, 2014.

(51) Int. Cl.
*A61M 5/142* (2006.01)
*F16B 45/00* (2006.01)
*F04B 43/12* (2006.01)

(52) U.S. Cl.
CPC ......... *A61M 5/14228* (2013.01); *F04B 43/12* (2013.01); *F16B 45/00* (2013.01)

(58) Field of Classification Search
CPC .................. A61M 5/14228; A61M 2205/12
See application file for complete search history.

(56) References Cited

U.S. PATENT DOCUMENTS

| 3,494,458 A | 2/1970 | Meierhoefer |
| 4,193,174 A | 3/1980 | Stephans |
(Continued)

FOREIGN PATENT DOCUMENTS

| CN | 201108641 | 9/2008 |
| EP | 1557187 | 7/2005 |
(Continued)

OTHER PUBLICATIONS

International Search Report for corresponding International Application No. PCT/US2015/027307 mailed on Jul. 24, 2015; 3 pages.
(Continued)

*Primary Examiner* — Aarti B Berdichevsky
(74) *Attorney, Agent, or Firm* — Patterson Thuente Pedersen, P.A.

(57) ABSTRACT

A pressure plate is configured to be coupled to a control module of an infusion pump. First and second securing hooks may extend away from a major surface of the pressure plate proximally to a first end. Each of the securing hooks may be structured to reversibly and hingedly couple to a hinge pin of the control module. An arch may extend away from the major surface proximally to a second transverse end and be structured to be received by a latch receptacle of the control module. The pressure plate may be secured to the control module by the securing hooks and arch. Each of the securing hooks may include a bearing surface configured to bear against a hinge pin when the pressure plate is secured to the control module, each bearing surface being parallel along the longitudinal axis with respect to the first major surface to within five degrees.

21 Claims, 5 Drawing Sheets

(56) References Cited

U.S. PATENT DOCUMENTS

| | | |
|---|---|---|
| 4,381,836 A | 5/1983 | Rivkin et al. |
| 4,451,693 A | 5/1984 | Vest |
| 4,559,038 A | 12/1985 | Berg et al. |
| 4,565,542 A | 1/1986 | Berg |
| 4,567,983 A | 2/1986 | Morris |
| 4,634,004 A | 1/1987 | Mortensen |
| 4,650,469 A | 3/1987 | Berg et al. |
| D294,733 S | 3/1988 | Peterson et al. |
| 4,802,601 A | 2/1989 | Pijanowski et al. |
| 4,867,738 A | 9/1989 | Mintz |
| D309,662 S | 7/1990 | Gorton |
| 4,944,485 A | 7/1990 | Daoud et al. |
| 5,017,192 A | 5/1991 | Dodge et al. |
| 5,106,366 A | 4/1992 | Steppe |
| 5,165,874 A | 11/1992 | Sancoff et al. |
| 5,181,910 A | 1/1993 | Scanlon |
| 5,213,483 A | 5/1993 | Flaherty et al. |
| 5,257,978 A | 11/1993 | Haber et al. |
| 5,336,174 A | 8/1994 | Daoud et al. |
| 5,336,190 A | 8/1994 | Moss et al. |
| 5,364,242 A | 11/1994 | Olsen |
| D353,667 S | 12/1994 | Tsubota et al. |
| 5,370,622 A | 12/1994 | Livingston et al. |
| 5,397,222 A | 3/1995 | Moss et al. |
| 5,425,173 A | 6/1995 | Moss et al. |
| 5,429,485 A | 7/1995 | Dodge |
| 5,437,642 A | 8/1995 | Thill et al. |
| 5,453,098 A | 9/1995 | Botts et al. |
| 5,482,446 A | 1/1996 | Williamson et al. |
| 5,485,408 A | 1/1996 | Blomquist |
| 5,531,697 A | 7/1996 | Olsen et al. |
| 5,531,698 A | 7/1996 | Olsen |
| 5,538,399 A | 7/1996 | Johnson |
| 5,540,561 A | 7/1996 | Johnson |
| 5,564,915 A | 10/1996 | Johnson |
| 5,567,119 A | 10/1996 | Johnson |
| 5,567,136 A | 10/1996 | Johnson |
| D376,848 S | 12/1996 | Zeilig et al. |
| 5,620,312 A | 4/1997 | Hyman et al. |
| 5,630,710 A | 5/1997 | Tune et al. |
| 5,647,854 A | 7/1997 | Olsen et al. |
| 5,658,252 A | 8/1997 | Johnson |
| 5,669,877 A | 9/1997 | Blomquist |
| 5,695,473 A | 12/1997 | Olsen |
| 5,755,691 A | 5/1998 | Hilborne |
| 5,772,409 A | 6/1998 | Johnson |
| 5,782,805 A | 7/1998 | Meinzer et al. |
| 5,788,671 A | 8/1998 | Johnson |
| 5,788,674 A | 8/1998 | McWilliams |
| 5,810,771 A | 9/1998 | Blomquist |
| 5,816,779 A | 10/1998 | Lawless et al. |
| 5,823,746 A | 10/1998 | Johnson |
| 5,879,143 A | 3/1999 | Cote et al. |
| 5,879,144 A | 3/1999 | Johnson |
| 5,904,668 A | 5/1999 | Hyman et al. |
| 5,928,196 A | 7/1999 | Johnson et al. |
| 5,935,099 A | 8/1999 | Peterson et al. |
| 5,935,106 A | 8/1999 | Olsen |
| 5,954,485 A | 9/1999 | Johnson et al. |
| 5,954,696 A | 9/1999 | Ryan |
| 5,993,420 A | 11/1999 | Hyman et al. |
| 6,024,539 A | 2/2000 | Blomquist |
| 6,056,522 A | 5/2000 | Johnson |
| 6,059,753 A | 5/2000 | Faust et al. |
| 6,077,055 A | 6/2000 | Vilks |
| 6,123,686 A | 9/2000 | Olsen et al. |
| 6,131,773 A | 10/2000 | Wade et al. |
| 6,202,708 B1 | 3/2001 | Bynum |
| 6,203,528 B1 | 3/2001 | Deckert et al. |
| 6,241,704 B1 | 6/2001 | Peterson et al. |
| 6,267,564 B1 | 7/2001 | Rapheal |
| D447,558 S | 9/2001 | Cartledge et al. |
| 6,374,876 B2 | 4/2002 | Bynum |
| 6,422,057 B1 | 7/2002 | Anderson |
| 6,475,180 B2 | 11/2002 | Peterson et al. |
| 6,742,992 B2 | 6/2004 | Davis |
| 7,150,735 B2 | 12/2006 | Hickle |
| 7,258,534 B2 | 8/2007 | Fathallah et al. |
| 7,347,836 B2 | 3/2008 | Peterson et al. |
| D586,463 S | 2/2009 | Evans et al. |
| 7,654,976 B2 | 2/2010 | Peterson et al. |
| D626,647 S | 11/2010 | Amborn et al. |
| 7,967,773 B2 | 6/2011 | Amborn et al. |
| D655,810 S | 3/2012 | Amborn et al. |
| 8,974,415 B2 | 3/2015 | Robert et al. |
| 2001/0010238 A1 | 8/2001 | Bynum |
| 2002/0183693 A1 | 12/2002 | Peterson |
| 2003/0014011 A1 | 1/2003 | Robert |
| 2008/0065007 A1 | 3/2008 | Peterson et al. |
| 2008/0065016 A1 | 3/2008 | Peterson et al. |
| 2008/0275425 A1 | 11/2008 | Strickler et al. |
| 2010/0094224 A1 | 4/2010 | Fathallah et al. |
| 2010/0211002 A1 | 8/2010 | Davis |
| 2011/0028899 A1 | 2/2011 | Beck et al. |
| 2011/0087165 A1 | 4/2011 | Amborn et al. |
| 2011/0313358 A1 | 12/2011 | Hariharesan et al. |
| 2012/0330238 A1 | 12/2012 | Robert et al. |
| 2013/0267899 A1 | 10/2013 | Robert et al. |
| 2014/0066850 A1 | 3/2014 | Robert et al. |
| 2014/0317929 A1 | 10/2014 | Robert et al. |

FOREIGN PATENT DOCUMENTS

| | | |
|---|---|---|
| EP | 2193815 | 6/2010 |
| WO | WO0051671 | 9/2000 |
| WO | WO2011008624 | 1/2011 |

OTHER PUBLICATIONS

Written Opinion for corresponding International Application No. PCT/US2015/027307 mailed on Jul. 24, 2015; 7 pages.

Application and File History for U.S. Appl. No. 13/443,390, filed Apr. 10, 2012, inventors Robert et al.

Pressure Plate and Free-flow Control for a CADD Infusion Pump Cassette, as shown in Figs. 7A and 7B of the application, available prior to Apr. 10, 2012, 1 page.

International Search Report dated Jul. 23, 2013 for International Application No. PCT/US2013/035393.

Application and File History for U.S. Appl. No. 14/325,989, filed Jul. 8, 2014, inventors Robert et al.

European Search Report for European Application No. 13775816.5 dated Apr. 1, 2016.

European Communication for European Application No. 13775816.5 dated Oct. 27, 2015.

INFUSION PUMP PRESSURE PLATE

CROSS REFERENCE TO RELATED APPLICATIONS

The present application is a National Phase entry of PCT Application No. PCT/US2015/027307, filed on 23 Apr. 2015, which claims priority to U.S. Provisional Patent Application No. 61/985,110, filed on 28 Apr. 2014, which are hereby fully incorporated herein by reference.

TECHNICAL FIELD

This disclosure relates to infusion pumps, and more particularly, to pressure plates configured for use with ambulatory infusion pumps.

BACKGROUND

Ambulatory infusion pumps are useful for providing a variety of drug therapies, and can be particularly beneficial for therapies that must be delivered over an extended period of time. Some aspects of ambulatory drug pumps are described for example in U.S. Pat. Nos. 4,559,038, 5,531,697, 5,658,252, 5,772,409, 5,823,746, and 5,879,144, the disclosures of which are incorporated by reference herein in their entireties.

The infusion pumps disclosed and described in the above-referenced patents may regulate the conveyance of fluid from a fluid reservoir to a patient. With infusion pumps like or similar to that of the aforementioned '038 patent, a fluid reservoir containing fluid for treating a patient may be held in a cassette having a pressure plate immediately adjacent to a pump control module. A tube for conveying the fluid may couple the fluid reservoir to the patient and provide a medium for conveying the fluid. A pump control module may include a pumping mechanism, having tube engaging members that are capable of engaging and sequentially squeezing the tube against the pressure plate of the cassette, in so-called "peristaltic"-type pumping action. The tube engaging members may include an expulsor and valves on opposite sides of the expulsor.

A variation of the infusion pump described in the aforementioned '038 patent may include a pump control module substantially as described above used in conjunction with a remote fluid reservoir, i.e., a fluid reservoir separate from the pump control module and not in a cassette that is directly coupled to the control module. Typically, in infusion pumps incorporating remote fluid reservoirs, the fluid reservoir may be secured on a holding apparatus, such as a pole, separate from the pump control module instead of in the cassette. The tube conveying the fluid from the remote fluid reservoir to the patient typically extends from the remote fluid reservoir, across a mechanically actionable portion or surface of the pump control module, and to the patient. In particular, in such an arrangement, the fluid-conveying tube may be disposed between the pump control module and a so-called "remote reservoir adapter" or "RRA" that includes a pressure plate, with tube engaging members of the control module squeezing the tube against the pressure plate to provide the aforementioned peristaltic-type pumping action.

While infusion pumps as described have been generally deemed by those in the medical arts to be advantageous in delivering fluids to patients reliably, some variation in delivery accuracy (with respect to volume of fluid delivered) has been observed with some known examples of pumps and pressure plates. It would therefore be desirable to improve pressure plate designs to reduce such variations and improve delivery accuracy.

SUMMARY

This disclosure relates to infusion pumps, and more particularly, to pressure plates configured for use with ambulatory and other infusion pumps.

In an illustrative but non-limiting example, the disclosure provides a pressure plate configured to be coupled to a control module of an infusion pump. The control module may be structured to receive the pressure plate along a mating side of the control module. The mating side may have two hinge pins disposed proximally to a first end of the mating side. The two hinge pins may be substantially co-linear along a hinge axis. The mating side also may have a latch receptacle disposed proximally to a second end of the mating side opposite the first end. The control module may include a latch mechanism associated with the latch receptacle.

The pressure plate may include a body, first and second securing hooks, an arch, and a fluid transport tube. The body of the pressure plate may have first and second major surfaces, a longitudinal axis and a transverse axis, first and second longitudinal sides, and first and second transverse ends. The first and second securing hooks may extend away from the first major surface of the body proximal the first transverse end. Each of the first and second securing hooks may be structured to reversibly and hingedly be coupled to a corresponding one of the two hinge pins. The arch may extend away from the first major surface of the body of the pressure plate proximal the second transverse end and be structured to be received by the latch receptacle of the mating side of the control module as the pressure plate is pivoted about the two hinge pins toward the control module. The arch further may be structured to be captured by the latch mechanism of the control module. The pressure plate may be secured to the control module by the securing hooks and arch when the arch is captured by the latch mechanism. The fluid transport tube may be disposed along the first major surface of the body of the pressure plate.

Each of the first and second securing hooks may include a bearing surface configured to bear against a corresponding one of the two hinge pins when the pressure plate is secured to the control module. Each bearing surface may face the first major surface of the body, and each bearing surface may be flat along the longitudinal axis along a bearing surface length of at least 1.40 mm, and parallel along the longitudinal axis with respect to the first major surface to within five degrees. In some instances, the bearing surface may be parallel along the longitudinal axis with respect to the first major surface to within one degree.

In some instances, each of the first and second securing hooks may further include a secondary surface making at least a 45 degree angle with respect to the bearing surface, with the secondary surface generally facing the corresponding hinge pin when the pressure plate is secured to the control module. In some cases, the secondary surface of each of the first and second securing hooks is substantially perpendicular to the bearing surface. In some cases, each of the first and second securing hooks of the pressure plate may further include a transition surface between the bearing surface and the secondary surface. When the two hinge pins of the control module to which the pressure plate is configured to couple have a hinge pin radius, the transition surface may be radiused such that a pin having the hinge pin radius is able to contact both the bearing surface and the secondary surface without contacting the transition surface. In some cases, the transition surface may have a radius not greater than the hinge pin radius but not less than 80%, or 90%, of the hinge pin radius.

In some instances, the hinge pins and latch receptacle of the control module to which the pressure plate is configured to couple are spaced apart by a nominal separation, and the first and second securing hooks are shaped and spaced-apart from the arch such that when the pressure plate is secured to the control module, each of the two hinge pins of the control module contacts only the bearing surface of the corresponding securing hook of the pressure plate.

In some instances, the first securing hook has a first width in the transverse direction and the second securing hook has a second width in the transverse direction different than the first width.

In some instances, the fluid transport tube provides a fluid path substantially parallel to the first major surface of the body of the pressure plate, with the fluid path extending completely to the first transverse end of the body.

In another illustrative but non-limiting example, the disclosure provides a pressure plate configured to be coupled to a control module of an infusion pump. The pressure plate may include a body having first and second major surfaces, a longitudinal axis and a transverse axis, first and second longitudinal sides, and first and second transverse ends; first and second pump-securing securing extensions projecting away from the first major surface of the body of the pressure plate adjacent the first transverse end, and an arch extending away from the first major surface of the body of the pressure plate adjacent the second transverse end, the arch configured to be captured by a latch of the control module.

Each of the first and second pump-securing securing extensions may be structured to reversibly and hingedly couple to a corresponding hinge pin of the control module. Each pump-securing extension may include a bearing surface, a secondary surface, and a transition surface. The bearing surface may be configured to bear against the corresponding hinge pin and face the first major surface of the body of the pressure plate. The bearing surface may be flat along the longitudinal axis and parallel along the longitudinal axis with respect to the first major surface to within five degrees, and in some cases, to within one degree. The secondary surface may make at least a 45 degree angle with respect to the bearing surface and generally face the corresponding hinge pin when the pressure plate is secured to the control module. The transition surface, disposed between the bearing surface and the secondary surface, may have a radius not greater than a hinge pin radius of the corresponding hinge pin but not less than 80% or 90% of the hinge pin radius. In some cases, the secondary surface of each of the first and second securing hooks may be substantially perpendicular to the bearing surface. In some cases, the pressure plate may further include a fluid transport tube disposed along the first major surface of the body of the pressure plate.

In yet another illustrative but non-limiting example, the disclosure provides a pressure plate configured to be coupled to a control module of an infusion pump. The control module may be structured to receive the pressure plate along a mating side of the control module. The control module may have two hinge pins and a latch mechanism disposed on the mating side. The hinge pins and latch mechanism may be spaced apart by a pump separation.

The pressure plate may include a body having first and second major surfaces, a longitudinal axis and a transverse axis, first and second longitudinal sides, and first and second transverse ends; first and second securing hooks extending away from the first major surface of the body of the pressure plate proximal the first transverse end; an arch extending away from the first major surface of the body of the pressure plate proximal the second transverse end; and a fluid transport tube disposed along the first major surface of the body of the pressure plate. Each of the first and second securing hooks may be structured to reversibly and hingedly couple to a corresponding one of the two hinge pins and the arch may be structured to be captured by the latch mechanism of the control module. The pressure plate may be secured to the control module by the securing hooks and arch when the arch is captured by the latch mechanism. The arch may be spaced-apart from the first and second securing hooks by a plate separation.

Each of the first and second securing hooks may have a hook shape that includes a bearing surface configured to bear against a corresponding one of the two hinge pins when the pressure plate is secured to the control module. Each bearing surface may face the first major surface of the body of the pressure plate and be flat along the longitudinal axis. Each bearing surface may be parallel along the longitudinal axis with respect to the first major surface to within five degrees, and in some cases, to within one degree.

The pressure plate and the control module may be structured such that relative longitudinal play between the pressure plate and the control module exists over a longitudinal range of motion when the pressure plate is secured to the control module via the securing hooks and the arch. The first and second securing hooks may be positioned relative to the body such that, and the hook shape of each of the first and second securing hooks may be provided such that, when the pressure plate is secured to the control module, each of the two hinge pins of the control module may contact only the bearing surface of the corresponding securing hook of the pressure plate at a contact point anywhere in a contact range that extends longitudinally in each direction by at least a pre-selected distance about a nominal contact point. Such longitudinal displacement of the contact point from the nominal contact point may be attributable to the combined variations of: (a) pump separation relative to a pump nominal separation, (b) plate separation relative to a plate nominal separation, and (c) longitudinal play over the longitudinal range of motion. In some instances, the pre-selected distance may be in a range between about 0.70 mm and about 1.00 mm. In some instances, each bearing surface is flat along a bearing surface length of at least about 1.40 mm.

In some instances, each of the first and second securing hooks may further include a secondary surface making at least a 45 degree angle with respect to the bearing surface and generally facing the corresponding hinge pin when the pressure plate is secured to the control module, and a transition surface between the bearing surface and the secondary surface. With each of the two hinge pins having a hinge pin radius, the transition surface of each of the first and second securing hooks may have a radius not greater than the hinge pin radius but not less than 80%, or 90%, of the hinge pin radius. In some cases, the secondary surface of each of the first and second securing hooks may be substantially perpendicular to the bearing surface.

In some instances, the first and second securing hooks may be spaced-apart from the arch by a separation within a range of at least about ±0.5 mm of a plate nominal separation. The first and second securing hooks may be shaped to achieve the result, in combination with the separation of the hooks from the arch within the range of at least about ±0.5 mm of the plate nominal separation, that when the pressure plate is secured to the control module, each of the two hinge pins of the control module contacts only the bearing surface of the corresponding securing hook of the pressure plate.

In still another illustrative but non-limiting example, the disclosure provides an infusion pump system comprising a control module and a pressure plate. The control module may be configured to pump fluid supplied from a reservoir and include a mating side, with two hinge pins disposed on the mating side. The control module also may have a latch mechanism disposed on the mating side, with the hinge pins and latch mechanism being spaced apart by a pump separation. The pressure plate may be configured to couple to the control module, and wherein the control module may be structured to receive the pressure plate along the mating side of the control module.

The pressure plate may include a body, first and second securing hooks, an arch, and a fluid transport tube. The body of the pressure plate may have first and second major surfaces, a longitudinal axis and a transverse axis, first and second longitudinal sides, and first and second transverse ends. The first and second securing hooks may extend away from the first major surface of the body proximal the first transverse end. Each of the first and second securing hooks may be structured to reversibly and hingedly be coupled to a corresponding one of the two hinge pins. The arch may extend away from the first major surface of the body of the pressure plate proximal the second transverse end and be structured to be received by the latch receptacle of the mating side of the control module as the pressure plate is pivoted about the two hinge pins toward the control module. The arch further may be structured to be captured by the latch mechanism of the control module. The pressure plate may be secured to the control module by the securing hooks and arch when the arch is captured by the latch mechanism. The fluid transport tube may be disposed along the first major surface of the body of the pressure plate such that when the pressure plate is secured to the control module, the fluid transport tube may be disposed between the pressure plate and the control module adjacent the mating side of the control module.

Each of the first and second securing hooks may include a bearing surface configured to bear against a corresponding one of the two hinge pins when the pressure plate is secured to the control module. Each bearing surface may face the first major surface of the body, and each bearing surface may be flat along the longitudinal axis along a bearing surface length of at least about 1.40 mm, and parallel along the longitudinal axis with respect to the first major surface to within five degrees. In some instances, the bearing surface may be parallel along the longitudinal axis with respect to the first major surface to within one degree. The first and second securing hooks may be spaced-apart from the arch and shaped such that when the pressure plate is secured to the control module, each of the two hinge pins of the control module contacts only the bearing surface of the corresponding securing hook of the pressure plate.

The above summary is not intended to describe each and every example or every implementation of the disclosure. The Description that follows more particularly exemplifies various illustrative embodiments.

BRIEF DESCRIPTION OF THE FIGURES

The following description should be read with reference to the drawings. The drawings, which are not necessarily to scale, depict examples and are not intended to limit the scope of the disclosure. The disclosure may be more completely understood in consideration of the following description with respect to examples in connection with the accompanying drawings, in which.

DESCRIPTION

The following description should be read with reference to the drawings, in which like elements in different drawings may be numbered in like fashion. The drawings, which are not necessarily to scale, depict selected examples and are not intended to limit the scope of the disclosure. Although examples of construction, dimensions, and materials may be illustrated for the various elements, those skilled in the art will recognize that many of the examples provided have suitable alternatives that may be utilized within a scope of novel and inventive subject matter hereof.

Figure 1:
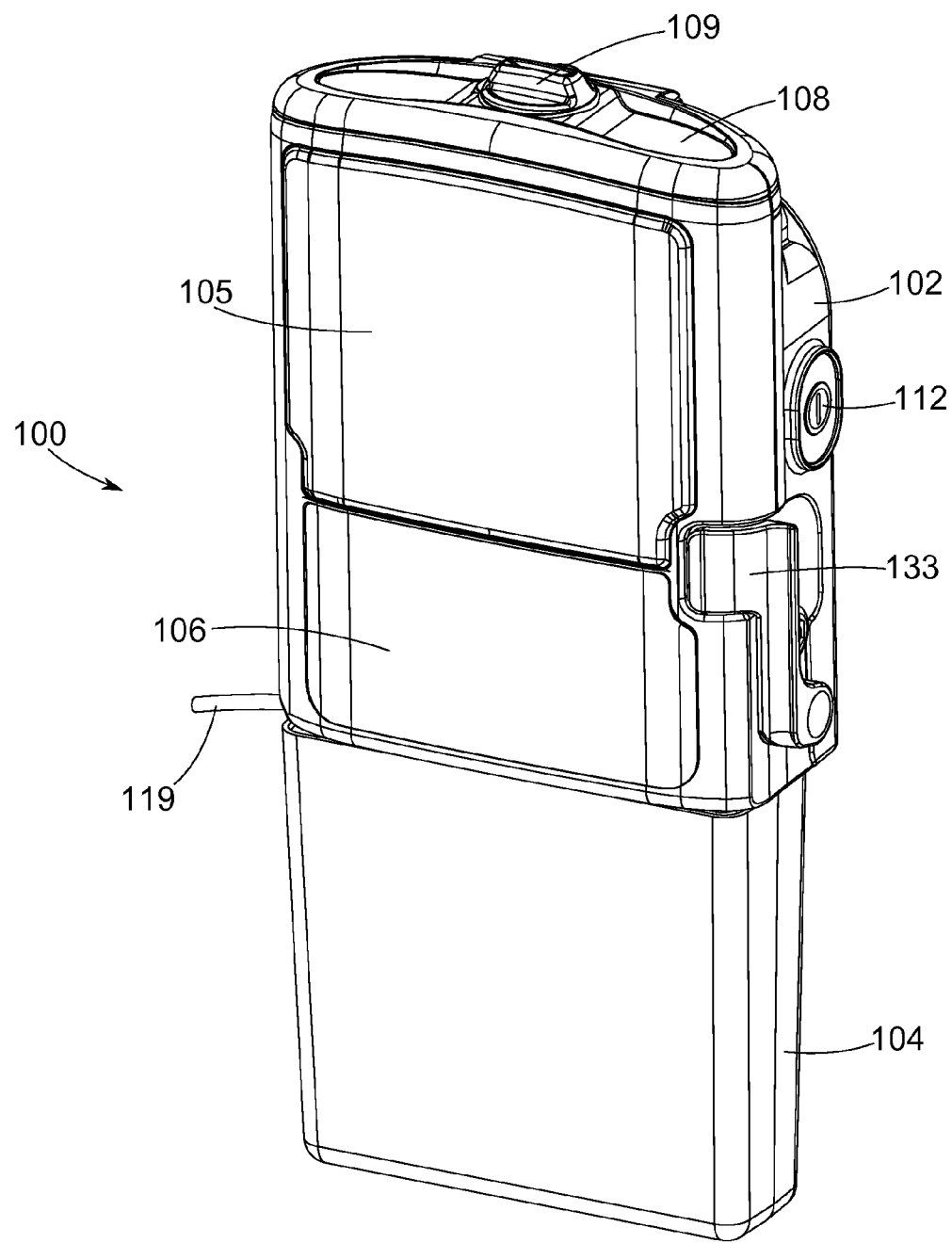
FIG. 1 is a schematic perspective view of an infusion pump system that includes a control module and a reservoir cassette.

FIG. 1 is a schematic perspective view of an illustrative infusion pump system 100 that includes a control module 102 and an optional reservoir cassette 104. Infusion pump system 100 may be a CADD® (Computerized Ambulatory Drug Delivery) Ambulatory Infusion Pump system from Smiths Medical ASD, Inc., although the teachings of the present disclosure are not limited to CADD® infusion pumps and may be practiced with any suitable infusion pump system.

Control module 102 of infusion pump system 100 may include a user interface having a display screen 105 and a control pad 106 (buttons, etc., of the control pad are not illustrated). Control module 102 may also include a battery door 108, including a knob 109 for locking and unlocking the door 108, which may cover a battery compartment in which batteries for powering the pump system 100 can be housed. In some examples, a combination battery and wireless communication module may be present approximately where battery door 108 is illustrated. Control module 102 may also include any or all of a power switch 112, and, visible in FIG. 2 but not FIG. 1: an input/output port 114 such as a USB port or other appropriate interface for connecting pump system 100 to a computer having software designed to interface with pump system 100, a power jack 116 for connecting a power cord for powering pump 100, and a remote dose cord jack 118 for connecting a remote dose cord that provides a way to activate patient-controlled administration of doses from pump system 100 or "PCA."

Infusion pump system 100 may include a replaceable reservoir cassette 104 connected to control module 102. In some illustrative examples, reservoir cassette 104 may house a reservoir containing medication to be delivered to a patient. Tubing 119 may extend from the cassette 104 and communicate with an infusion set or catheter (not shown) to deliver the medication to the patient. The control module 102 can be used to control the flow of medication from the cassette. One example of such a cassette is the CADD® Medication Cassette Reservoir from Smiths Medical ASD, Inc., though other cassettes can be used in other examples.

Figure 2:
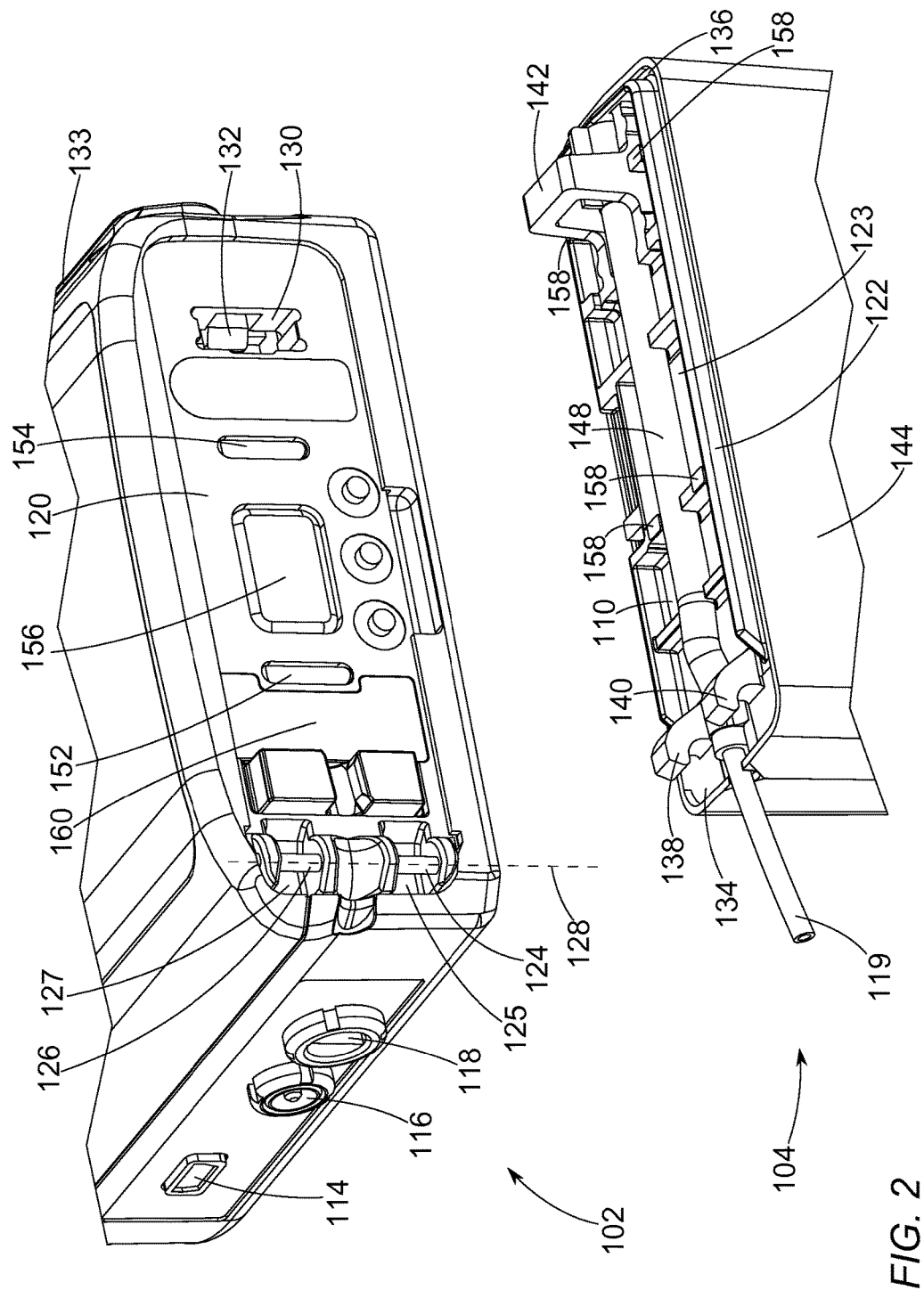
FIG. 2 is a schematic partial perspective view of the infusion pump system of FIG. 1 with the reservoir cassette separated from the control module.

FIG. 2 is a schematic partial perspective view of infusion pump system 100 with reservoir cassette 104 separated from control module 102, and rotated to provide views of their mating structures. Control module 102 and reservoir cassette 104 may be configured to reversibly mate or connect at a mating side 120 and pressure plate 122, respectively.

The mating side 120 of control module 102 may include two hinge pins 124 and 126 proximally to a first end of the mating side, although in other examples a single hinge pin or more than two hinge pins may be employed. Hinge pins 124 and 126 may be essentially identical in structure, or they may differ. Hinge pins 124 and 126 may be co-linear along a hinge axis 128, which may be substantially traverse or perpendicular to a longitudinal axis of mating side 120. Hinge pins 124 and 126 may be disposed in hinge wells 125 and 127, respectively, which may be essentially identical in structure, or they may differ. In some examples, hinge wells 125 and 127 may have different transverse widths.

The mating side 120 of control module 102 may include a latch receptacle 130 disposed proximally to a second end of the mating side opposite the first end. The control module 102 may include a latch mechanism 132 associated with the latch receptacle 130, and a latch lever 133 to allow a user to manipulate the latch mechanism.

Pressure plate 122 of reservoir cassette 104 generally includes a body 123 having first 110 and second major surfaces (top and bottom, respectively, relative to FIG. 2), a longitudinal axis and a transverse axis, first and second longitudinal sides, and first 134 and second 136 transverse ends. The pressure plate 122 may include first and second securing hooks 138, 140 extending away from the first major surface 110 of the body 123 proximal the first transverse end 134. Each of the first and second securing hooks 138, 140 may be structured to reversibly and hingedly couple to a corresponding one of the two hinge pins 124, 126. In some examples, pressure plates include securing hooks in one-to-one correspondence with the number of hinge pins of the control modules to which they are designed to mate. However, in some cases the numbers of securing hooks and hinge pins are not necessarily required to correspond. For example, in some examples a pressure plate may include two securing hooks that both couple to a single hinge pin that is long enough to accommodate both hooks. In the present disclosure, any suitable arrangements of securing hook(s) and hinge pin(s) are contemplated.

In some examples, transverse widths of securing hooks and hinge wells may tend to aid in ensuring or preventing compatibility of pressure plates and control modules. For example, a first control module may have two hinge wells of a relatively narrow first width, and a second control module may have two hinge wells of a relatively wide second width. A first pressure plate variety having narrower hooks corresponding to the relatively narrow first width may be compatible with both the first control module and the second control module, whereas a second pressure plate variety having wider hooks corresponding to the relatively wide second width may be compatible only with the second control module, and not with the first control module. In another example, first and second hinge wells of a third control module may have different widths, and first and second securing hooks of some exemplary pressure plates may have different widths corresponding to the different widths of the hinge wells of the third control module. Some examples of pressure plates of the present disclosure may feature securing hooks having the largest practical widths that match the widths of the corresponding hinge wells of the control unit(s) to which they are intended to mate, in order to minimize or eliminate undesirable transverse play or movement that otherwise might be allowed between them by relatively narrower securing hooks coupled to relatively wider hinge wells. Any suitable configuration of securing hook widths may be used on pressure plates to affect compatibility and stability with control units.

Pressure plate 122 also may include an arch 142 extending away from the first major surface 110 of the body 123 proximally to the second transverse end 136. The arch 142 and latch receptacle 130 of the mating side 120 of the control module 102 may be structured such that the arch may be received by the latch receptacle as the pressure plate is pivoted about the two hinge pins 124, 126 toward the control module. The arch 142 may be structured to be captured by the latch mechanism 132 of the control module 102 and drawn toward mating side 120 of the module by the latch mechanism 132. When the arch 142 is captured by the latch mechanism 132 and the first and second securing hooks 138, 140 are coupled to the hinge pins 124, 126, the pressure plate 122 may be secured to the control module 102 by the securing hooks and arch. The latch mechanism 132 of the control module 102 may be configured to exert a longitudinal force on the pressure plate 122 via cooperative engagement with the arch 142. For example, as the latch mechanism 132 engages arch 142 of the pressure plate 122, the latch mechanism 132 may exert a force on the pressure plate 122 toward the first transverse end (or alternately, toward the second transverse end). Contact forces between the arch 142 and a wall of the latch receptacle 130 may counter the force exerted by the latch mechanism 132, with the paired forces working together to stabilize the pressure plate 122 relative to the control module 102 in the longitudinal direction.

Pressure plate 122 may be formed from any suitable material. In some examples, pressure plates are formed from polycarbonate material, though other materials may be used. Pressure plate 122 may be joined, for example via bonding or ultrasonic welding, with a casing 144 (which may also be formed primarily of polycarbonate material) to together provide a housing of reservoir cassette 104. Reservoir cassette 104 may house a medicament container (not shown), which may be, for example, a vinyl bag. A fluid transport tube 148 may be attached to or integrally formed with the medicament container to provide a fluid path from the medicament container to a patient, via, for example, tubing 119 connected to tube 148. Fluid transport tube 148 may be substantially longitudinally disposed along the first major 110 surface of the body 123 of pressure plate 122, and may provide a fluid path that is substantially parallel to the first major 110 surface. The fluid path provided by fluid transport tube 148 may extend essentially completely to the first transverse end of the body 123.

When reservoir cassette 104 is secured to control module 102, as illustrated in FIG. 1, the control module may pump fluid from the medicament container through fluid transport tube 148 by way of a peristaltic-type pump mechanism. Tube engaging members visible in FIG. 2 may include valves 152, 154, and expulsor 156, which may engage and squeeze (compress) the fluid transport tube 148 against the pressure plate 122 in a coordinated manner to effect a peristaltic-type pumping action, as described, for example, in aforementioned U.S. Pat. No. 4,559,038.

Figure 3:
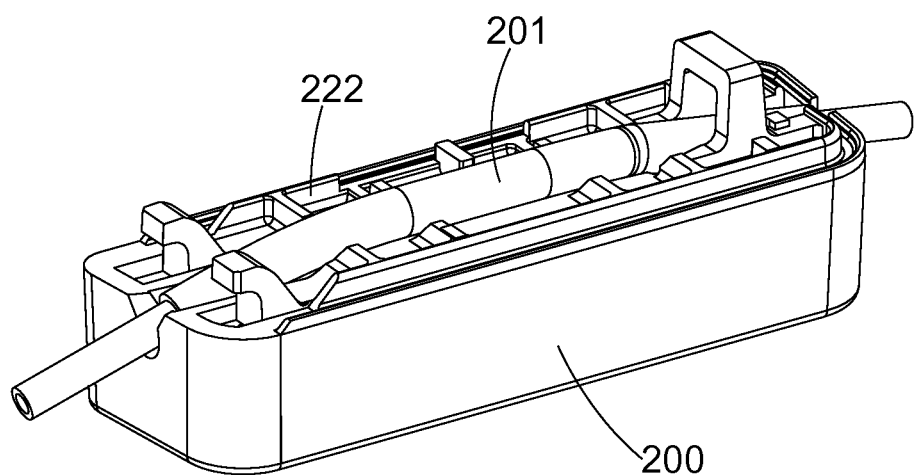
FIG. 3 is a schematic perspective view of a remote reservoir adapter.

In an alternative configuration practiced in some illustrative examples, an infusion pump may deliver fluid from a reservoir that is remote, or separate from the control module of the pump, such as an IV bag. FIG. 3 is a schematic perspective view of a remote reservoir adapter ("RRA") 200 that may be employed in such examples. Tubing 201 may extend from the IV bag (not illustrated) or other remote reservoir to RRA 200 and then to an infusion set or catheter, and flow of medication through the tubing can be controlled by control module 102 coupled to RRA 200 in a manner similar to the coupling of control module 102 to cassette 104 as described with reference to FIG. 1. An example of an RRA may be provided as a component of a CADD® Administration Set from Smiths Medical ASD, Inc. RRA 200 may include a pressure plate 222 similar to pressure plate 122 of reservoir cassette 104.

In the present disclosure, the term "pressure plate" may refer to a structure or combination of structures that cooperate, when coupled to a pump control module, to maintain a substantially fixed surface at a nominal separation from the pump control module, against which tube engaging members of the pump control module may engage and squeeze a fluid transport tube that is disposed between the pressure plate and the pump control module. A remote reservoir adapter such as RRA 200 may be monolithically formed and pressure plate 222 may be integrally incorporated into the monolithic structure of RRA 200, but it is not necessary that a pressure plate be integrally formed with an RRA or any other device of which it may be a part. For example and as described elsewhere herein, a reservoir cassette 104 may include a pressure plate 122 and a casing 144 that are separately formed and then subsequently joined. Generally, any improvements to pressure plates described in the present disclosure may apply to pressure plates of cassette reservoirs, RRAs, or any other appropriate pressure plates or similar devices that are intended to be coupled, or latched, to corresponding control modules as described herein.

Referring again to FIGS. 1 and 2, and as discussed, in part, in aforementioned U.S. Pat. No. 4,559,038, spacing between the pressure plate 122 and the mating side 120 of the control module 102 may influence the peristaltic pumping action with regard to efficiency, accuracy, precision, and the like. More particularly, it may be desirable to control the spacing between the pressure plate 122 and the mating side 120 at and around the locations where the valves 152, 154 and expulsor 156 engage the fluid transport tube 148. To help maintain appropriate spacing between the pressure plate 122 and the control module 102, the pressure plate may be designed with standoffs or datums 158 where the pressure plate is intended to contact the mating side 120 of the control module. Engagement of the securing hooks 138, 140 of the pressure plate 122 with hinge pins 124, 126 of the control module 102, and of the arch 142 with the latch receptacle 130 and latch mechanism 132 of the control module may retain the pressure plate firmly against the mating side 120 of the control module, with contact between the datums 158 and the mating side defining, in part, the minimum spatial separation therebetween.

Since their introduction to the market, ambulatory infusion pumps incorporating many of the features illustrated in FIGS. 1-3 and described in corresponding portions of this disclosure have enjoyed considerable therapeutic, technical, and commercial success. Nonetheless, opportunities for improved performance remain. With known control module and reservoir cassette combinations, variations of a few percent in drug delivery volume have been observed, both between different cassettes, and with the use of the same cassette, for example when that same cassette is shifted in position relative to the control module along the longitudinal axis within a small range of motion permitted by the mechanism securing the cassette to the module. Not only is drug delivery volume affected, but also affected is the pressure in the fluid delivery tube measured by a downstream occlusion sensor 160 of the control module 102, which may lead to false alarms. Reducing variations in pump performance has been the object of concerted investigations over the years, sometimes with little success. The present disclosure describes improvements in pressure plate design consistently observed to aid in improving delivery accuracy and in reducing variations in measured pressure in fluid delivery tubes.

Figure 4:
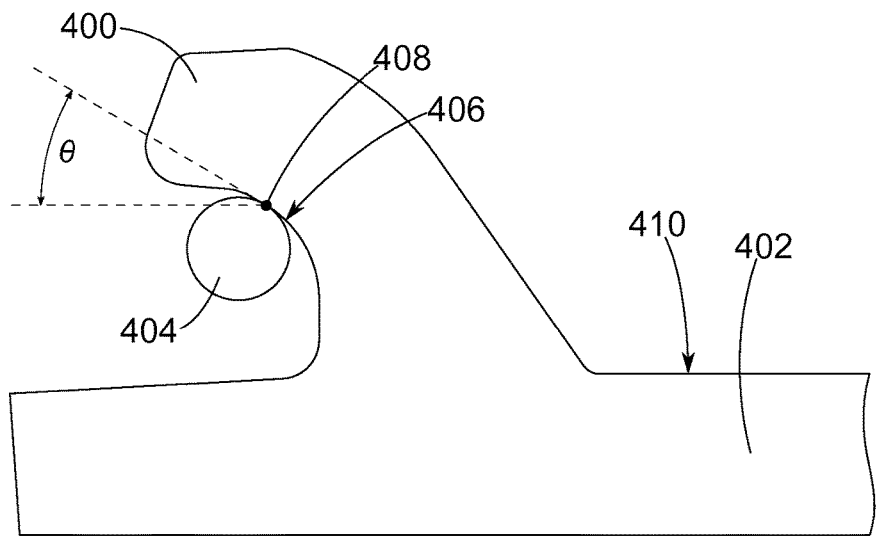
FIG. 4 is a schematic partial elevation view of a securing hook of a known pressure plate engaged with a corresponding hinge pin.

To better appreciate the improvements embodied in pressure plates of the present disclosure, we further contemplate aspects of currently known pressure plates. FIG. 4 is a schematic partial elevation view of a securing hook 400 of a known pressure plate 402 engaged with a corresponding hinge pin 404. The hinge pin 404 may generally contact a bearing surface 406 of the securing hook 400 at a contact point 408. (Note that generally the system of control module and pressure plate 402 may be designed with a degree of interference between securing hook 400 and hinge pins 404 to ensure secure contact therebetween.) The bearing surface 406 of known pressure plate 402 makes an angle $\theta$ with respect to the first major surface 410 of the pressure plate at the contact point 408. In known pressure plates, the angle $\theta$ generally is about 30 degrees, or between about twenty degrees and forty degrees. In some cases, the angle $\theta$ may vary with position (e.g., from left to right relative to FIG. 4) along bearing surface 406. The angled or curved shape of bearing surface 406 may be designed to assist coupling of securing hook 400 with hinge pin 404 as a cassette or RRA is coupled to a control module. Angles $\theta$ in the range of about 20 degrees to about 40 degrees may contribute to a more "open" shape for the securing hooks to provide a larger target opening for receiving a hinge pin as the parts are brought together.

The specific actual position of contact point 408 along bearing surface 406 of securing hook 400 with hinge pin 404 generally may affect the separation between the control module (of which hinge pin 404 is a component; not shown) and the first major surface 410 of the pressure plate. Such separation, in turn, may negatively affect delivery accuracy of infusion pump system 100 or cause undesirable variation in measured pressure in an associated fluid delivery tube. While ideally different control modules and different pressure plates might all have precisely identical dimensions, and the position of contact point 408 along bearing surface 406 might then be expected to be consistently identical in all combinations, in actual practice dimensions of manufactured parts vary (such as the distances between securing hooks and arches of pressure plates produced from different production lines), which may result in varying positions of contact points, and correspondingly, the separations between the control modules and the first major surfaces of the pressure plates.

In the absence of other considerations, it might be expected that a contact point 408 that is further to the left (relative to FIG. 4) on bearing surface 406 would result in a larger separation between control module and pressure plate, as compared with a contact point that is further to the right, due to the angle $\theta$ that the bearing surface 406 makes with the first major surface 410. However, there are additional factors to consider. As described elsewhere herein, for example, pressure plates may be designed and manufactured with reference locations such as datums 158 with the intent of defining the separation between the pressure plates and control modules. In such cases so constrained by contact between the datums and the mating side of the control module, left-right shifting of contact point 408 may result in decreases and increases in contact forces between the securing hook 400 and hinge pin 404, as the securing hook resiliently flexes. The variation of contact forces may then affect the separation between control module and pressure plate at other locations along the interface therebetween. Generally speaking, the separation between control module and pressure plate is determined by multiple considerations, including the hinge pin contact point on the bearing surface, the datums, flexure of the pressure plate, and so on. Experimentally (for example as described in one or more examples of this disclosure), it has now been determined that pump performance can be sensitive to the shape of the bearing surfaces of securing hooks, regardless of the exact details of the mechanism(s) responsible for such variations in pump performance. In some cases, improved performance has been observed when the angle between bearing surface and major surface (angle $\theta$ of FIG. 4) is reduced such that the bearing surface is flat and substantially parallel to the major surface of the pressure plate.

Figure 5:
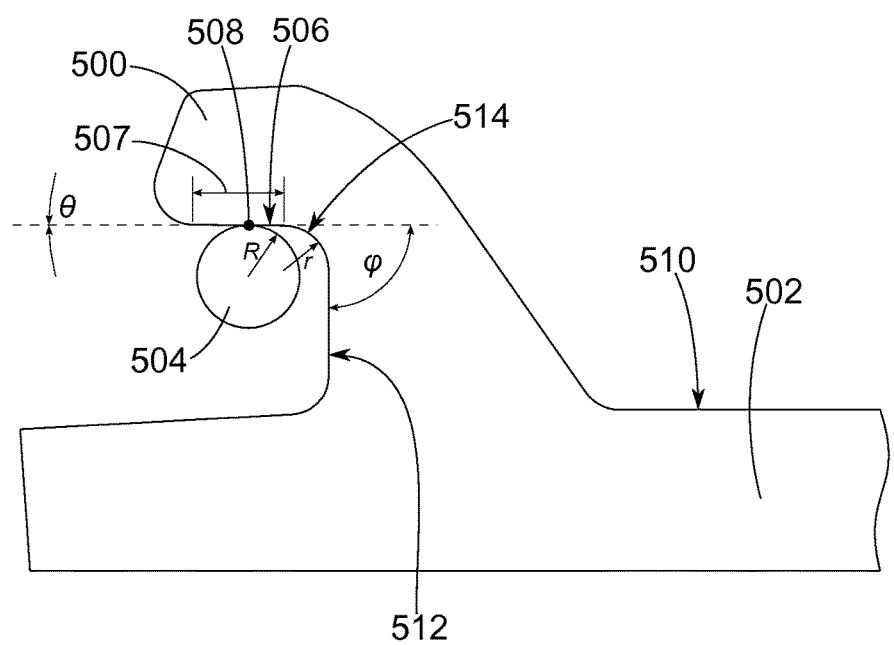
FIG. 5 is a schematic partial elevation view of an example of an improved securing hook of a pressure plate engaged with a corresponding hinge pin.

FIG. 5 is a schematic partial elevation view of an improved securing hook 500 of the present disclosure that includes features that, when incorporated into a pressure plate, have been empirically observed to advantageously result in more precise delivery volumes from an infusion pump system similar to pump system 100. Improved securing hook 500 may be incorporated as part of any suitable pressure plate, such as pressure plates 122 and 222 of FIGS. 2 and 3. An improved pressure plate of the present disclosure may include two or any other suitable quantity of improved securing hooks configured like hook 500. Securing hook 500 of improved pressure plate 502 includes a bearing surface 506 having a bearing surface length 507 configured to bear against a corresponding hinge pin 504 at a contact point 508 when the pressure plate is secured to the control module of hinge pin 504. Bearing surface length 507 may have any suitable value. The bearing surface length 507 may be at least about 1.40 mm, 1.5 mm, 1.6 mm, 1.7 mm, 1.8 mm, 1.9 mm, 2 mm, or any other suitable value. Bearing surface 506 faces the first major surface 510 of the body of the pressure plate 502, may be flat along the longitudinal axis of the pressure plate, and may be parallel along the longitudinal axis with respect to the first major surface to within one degree (angle $\theta \leq 1$ degree). In some examples, the bearing surface 502 may be parallel along the longitudinal axis with respect to the first major surface 510 to within one-half or one-quarter degree (angle $\theta \leq \frac{1}{2}$ or $\frac{1}{4}$ degree). In some examples, the bearing surface 502 may be parallel along the longitudinal axis with respect to the first major surface 510 to within two, three, four, or five degrees (angle $\theta \leq 2$, 3, 4, or 5 degrees). Because bearing surface 506 is substantially parallel to first major surface 510 of the body of pressure plate 502, it appears that the precise location of contact point 508 between the bearing surface and hinge pin 504 affects the relative mechanical forces and separation between the pressure plate 502 and hinge pin (and hence, control module) significantly less, as compared to the greater sensitivity of the configuration of the example of FIG. 4 to the location of contact point 408.

Securing hook 500 may include a secondary surface 512 generally facing the corresponding hinge pin 504. Secondary surface 512 may be substantially flat and may make at least a 45 degree angle with respect to the bearing surface 506 (angle $\phi \geq 45$ degrees). In some examples, the secondary surface may be substantially perpendicular to the bearing surface (i.e., angle $\phi \approx 90$ degrees, as illustrated in FIG. 5). Securing hook 500 may be dimensioned and shaped such that hinge pin 504 will not normally contact the hook other than at bearing surface 506. If in some cases, however, variations in manufacturing tolerances allow the hinge pin 504 to contact the secondary surface 512, steeper angles of the secondary surface 512 relative to the bearing surface 506 (i.e., larger values for $\phi$) may help prevent the pin from sliding along the secondary surface, which could result, if occurring when $\phi$ is smaller, in drawing the pressure plate closer to the control module.

Securing hook 500 may further include a transition surface 514 between bearing surface 506 and secondary surface 512. The transition surface 514 may be shaped to prevent potential contact of hinge pin 504 with the transition surface, to obviate the possibility of the pin sliding along the transition surface, which could result in drawing the pressure plate closer to the control module. The transition surface 514 may be shaped or radiused such that a pin having the same radius R as hinge pin 504 may be placed such that it is able to contact both bearing surface 506 and secondary surface 512 without contacting the transition surface. A transition surface 514 radiused as such may follow a circular arc having a radius r that is not greater than the radius R of the hinge pin 504 ($r \leq R$), or it may follow a non-circular curve.

In some illustrative examples, a transition surface 514 may follow a circular arc having a radius r that is not greater than the radius R of the hinge pin 504 but not less than about 80% of the hinge pin radius (0.8 $R \leq r \leq R$), or about 90% of the hinge pin radius (0.9 $R \leq r \leq R$). It may be desirable to avoid very small radiuses (i.e., $r \ll R$) for the transition surface 514, as such small radiuses may tend to weaken the securing hook 500 relative to examples not exhibiting such small radiuses. Securing hooks of the present disclosure may feature any suitable combination of angle $\phi$ and radius r.

In some examples where the transition surface 514 follows a non-circular curve, the non-circular curve may have a local radius not greater than hinge pin radius R everywhere, it may have a local radius not greater than hinge pin radius R at least at one location along the curve, it may have an average radius along the curve not greater than R, or it may have any other suitable shape that avoids contact with a pin of radius R when such pin is contacting both a bearing surface and a secondary surface.

In some examples, a securing hook 500 may include essentially no transition surface between bearing surface 502 and secondary surface 512, or the extent of such a transition surface may be considered essentially to be vanishingly or exceedingly small.

In some illustrative examples of the present disclosure, pressure plates may be structured such that, when secured to compatible control modules, the hinge pins of the control modules only contact the bearing surfaces of the securing hooks of the pressure plates, and do not contact the secondary surfaces or transition surfaces of the securing hooks. The bearing surfaces of such pressure plates may be substantially parallel or nearly parallel to first major surfaces of the pressure plates. When so structured, the separation between control module and pressure plate may be insensitive to the particular point(s) of contact between the hinge pin(s) and the securing hook(s). In some examples, pressure plates may be designed to allow for manufacturing variations in certain dimensions that still result in finished pressure plates that only contact hinge pins of control modules at the bearing surfaces of the securing hooks. Such an example is illustrated in FIG. 6, which is a schematic partial elevation view of an improved pressure plate 622 of the present disclosure showing features proximal the first 634 and second 636 transverse ends of the plate.

Figure 6:
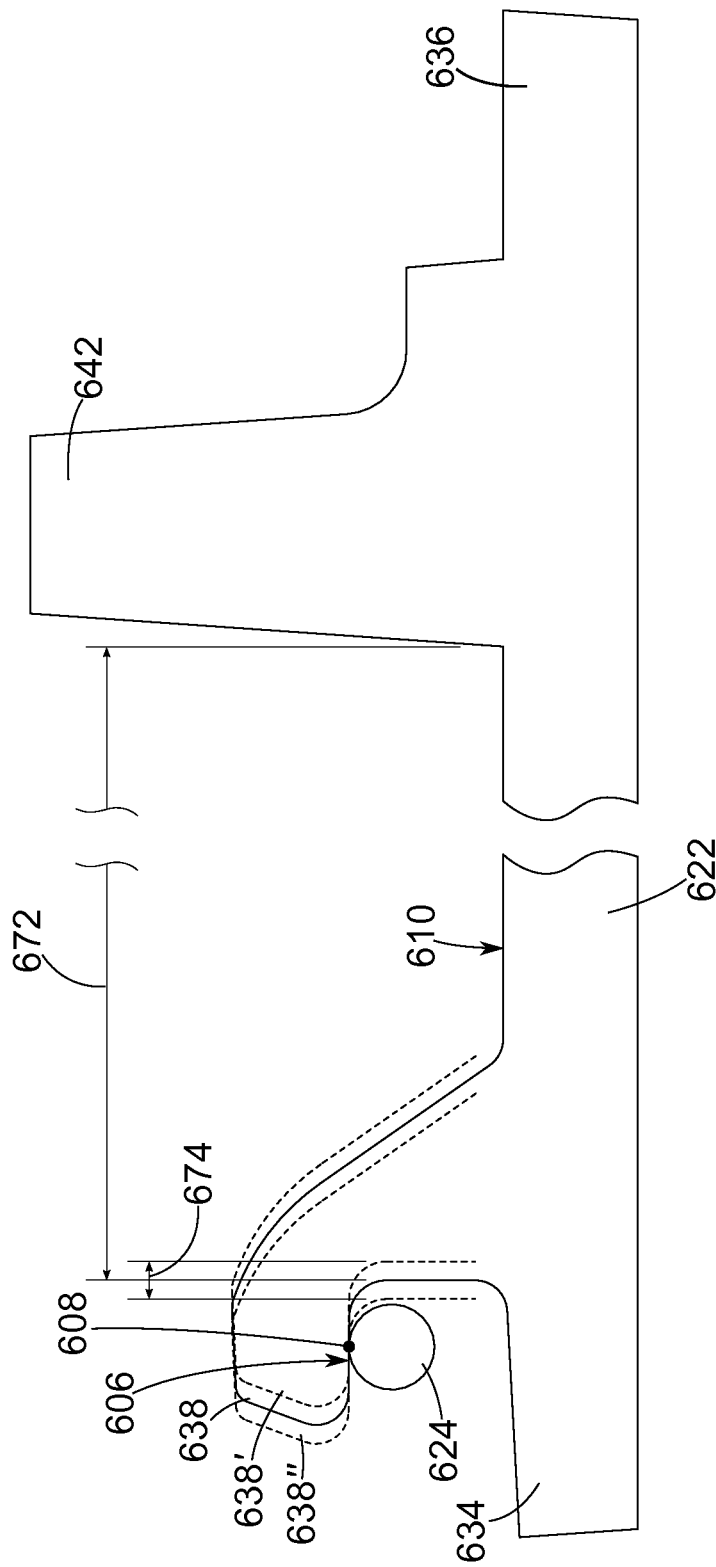
FIG. 6 is a schematic partial elevation view of an improved pressure plate, and depicting relative positions between the example of the improved securing hook engaged with the corresponding hinge pin of FIG. 5.

As illustrated in FIG. 6, the securing hooks (hook 638 and any other hooks, which may include any or all features, or similar features, of securing hook 500 of FIG. 5) of pressure plate 622 may be spaced apart from the arch 642 of the pressure plate by a plate nominal separation 672. In some instances, the plate nominal separation may be approximately 6.5 cm, but this example is not limiting. The plate nominal separation 672 may relate to a pump nominal separation between hinge pins (such as pins 124 and 126 shown in FIG. 2) and a latch receptacle (such as receptacle 130 shown in FIG. 2). The plate nominal separation 672 may relate to the pump nominal separation such that when the pressure plate 622 is secured to a control module having the pump nominal separation, each of the hinge pin(s) (represented by pin 624) of the control module contacts, at contact point 608, only the bearing surface 606 of the corresponding securing hook 638 of the pressure plate. Furthermore, the securing hook(s) 638 may be shaped and dimensioned such that if the actual plate separation between the securing hook(s) and the arch 642 is different from the plate nominal separation 672 within an allowable range 674 such as about ±0.10 mm, about ±0.2 mm, about ±0.13 mm, or any other suitable selected value (such difference being due to manufacturing variations or any other cause), each hinge pin 624 of the control module still contacts only the bearing surface 606 of the corresponding securing hook. Another source of potential variation of the actual location of contact point 608 where hinge pin 624 contacts securing hook 638 may be the difference between the actual pump separation and pump nominal separation. Yet another source of potential variation of the actual location of contact point 608 where hinge pin 624 contacts securing hook 638 may be relative longitudinal play over a longitudinal range of motion between the control module and the pressure plate 622 when the pressure plate is secured to the control module via the securing hooks and the arch 642. The position of securing hook 638 (and any novel securing hook of the present disclosure) on the body of pressure plate 622, and the hook shape of securing hook 638, may be provided such that when the pressure plate 622 is secured to the control module, each of the two hinge pins 624 of the control module contacts only the bearing surface 606 of the corresponding securing hook of the pressure plate at a contact point 606, where the contact point falls anywhere in a contact range that extends longitudinally in each direction by at least a pre-selected distance about a nominal contact point. The pre-selected distance may have any suitable value, and may be in a range between about 0.70 mm and about 1.00 mm. The bearing surface 606 may be flat along a bearing surface length that is at least about 1.40 mm, about 1.5 mm, about 1.6 mm, about 1.7 mm, about 1.8 mm, about 1.9 mm, about 2 mm, or any other suitable value. The bearing surface length may, in some cases, be twice or approximately twice the pre-selected distance, but this is not necessary. The longitudinal displacement of the contact point from the nominal contact point may be attributable to the combined variations of: (a) pump separation relative to a pump nominal separation, (b) plate separation relative to a plate nominal separation, and (c) longitudinal play over the longitudinal range of motion. Securing hooks so shaped may beneficially contribute toward maintaining consistent separation between control modules and pressure plates, leading to more consistent pump performance.

In FIG. 6, examples of additional phantom hooks 638' and 638" represent the position of hook 606 in cases of shorter or longer hook-to-arch separation, respectively. In all of the examples represented by 638, 638' and 638", the hinge pin 624 contacts the respective hook only on its bearing surface 606. When, as illustrated, bearing surface 606 is substantially parallel to first major surface 610 of pressure plate 622, the particular location of the contact point 608 on bearing surface 606, which varies as the actual securing hook to arch separation varies, may be expected to have relatively little or negligible influence on the separation between control module and pressure plate, as compared to a known configuration such as that of FIG. 4 where the point of contact may vary up-and-down the bearing surface 406 (i.e., away-from-and-toward the first major surface 410) as the hook to arch separation varies. Thus the configuration of FIG. 6 may contribute to more consistent pump performance. While different relative positions of pin 624 to hooks 638, 638' and 638" may be illustrated in FIG. 6 as being attributable to variations in plate separation, those skilled in the art may easily perceive that such difference may also result from variations in pump separation, longitudinal play, and/or combinations of the three factors.

As illustrated in FIG. 6, contact point 608 may represent a nominal contact point relative to securing hook 638, which may be nominally located relative to hinge pin 624. Relative to phantom hooks 638' and 638", contact point 608 may represent contact points that are not nominal contact points, but are located in the corresponding contact ranges extending longitudinally in each direction by at least a pre-selected distance about the nominal contact point of each hook.

Example 1:

Delivery accuracy was measured for a CADD® Legacy Pump coupled with commercially-available 100 ml Non-Flowstop CADD® Medication Cassette Reservoirs. The volume of liquid (water) delivered by the pump under a standard control program was measured in two positions (at ends of a longitudinal range of motion of longitudinal play) for cassettes latched to the control unit (the CADD® Legacy Pump). In a first position, a cassette was shifted as far left (relative to the control unit, viewed from the orientation of FIG. 1) as possible, without using excessive force, before engaging the latch. In a second position, a cassette was shifted as far right as possible, without using excessive force, before engaging the latch. Each of ten cassettes was tested six times each (three times each left-shifted and right-shifted), with the cassette unlatched from the control unit after each test.

A statistically significant difference in delivery volume was observed when comparing the left and right shift positions. The average difference between left and right positions was 3.5%, with the system delivering more liquid when the cassettes were shifted to the left then when shifted to the right.

Example 2:

Delivery accuracy was measured for a CADD® Legacy Pump coupled with commercially-available 100 ml Non-Flowstop CADD® Medication Cassette Reservoirs. The volume of liquid (water) delivered by the pump under a standard control program was measured in three positions for cassettes latched to the control unit. In a first position, a cassette was shifted as far left as possible, without using excessive force, before engaging the latch. In a second position, a cassette was shifted as far right as possible, without using excessive force, before engaging the latch. In a third, unbiased, position, a cassette was attached and latched to the control unit without emphasis placed either to the left or right side. Each of three cassettes was tested nine times each (three times each left-shifted, right-shifted, and unbiased), with the cassette unlatched from the control unit after each test.

A statistically significant difference in delivery volume was observed when comparing the left and right shift positions. The average difference between left and right positions was 4.0%, with the system delivering more liquid when the cassettes were shifted to the left then when shifted to the right. In the unbiased position, on average the cassettes delivered closer to the left-shifted position than the right-shifted position. The average delivery volume difference between the unbiased position and the left and right shifted positions were +1.1% and −2.9%, respectively.

Example 3:

Delivery accuracy was measured for a CADD® Legacy Pump coupled with five 100 ml Non-Flowstop CADD® Medication Cassette Reservoir that were modified to create longer flat bearing surfaces on their securing hooks, similar to the bearing surfaces of FIG. 5 described in the present disclosure. The volume of liquid (water) delivered by the pump under a standard control program was measured in two positions for cassettes latched to the control unit. In a first position, a cassette was shifted as far left (relative to the control unit, viewed from the orientation of FIG. 1) as possible, without using excessive force, before engaging the latch. In a second position, a cassette was shifted as far right as possible, without using excessive force, before engaging the latch. In a third, unbiased, position, a cassette was attached and latched to the control unit without emphasis placed either to the left or right side. Each of the modified cassettes was tested nine times each (three times each left-shifted, right-shifted, and unbiased), with the cassette unlatched from the control unit after each test.

A statistically significant difference in delivery volume was observed when comparing the left and right shift positions. The average difference between left and right positions was 0.8%, with the system delivering more liquid when the cassettes were shifted to the left then when shifted to the right. This average difference of 0.8% may be considered to represent a considerable improvement over the average differences of 3.5% and 4.0% of Examples 1 and 2, respectively.

The disclosure should not be considered limited to the particular examples described herein, but rather should be understood to cover all aspects of the disclosure and equivalents thereof. Various modifications, equivalent processes, as well as numerous structures to which the disclosure can be applicable will be readily apparent to those of skill in the art upon review of the instant specification.

What is claimed is:

1. A pressure plate configured to couple to a control module of an infusion pump, the control module being structured to receive the pressure plate along a mating side of the control module, the control module having two hinge pins disposed on the mating side, the control module also having a latch mechanism disposed on the mating side, the hinge pins and latch mechanism being spaced apart by a pump separation, the pressure plate comprising:
   a body having first and second major surfaces, a longitudinal axis and a transverse axis, first and second longitudinal sides, and first and second transverse ends;
   first and second securing hooks extending away from the first major surface of the body proximal the first transverse end, each of the first and second securing hooks structured to reversibly and hingedly couple to a corresponding one of the two hinge pins;
   an arch extending away from the first major surface of the body proximal the second transverse end, the arch structured to be captured by the latch mechanism of the control module, the arch spaced-apart from the first and second securing hooks by a plate separation, the pressure plate being secured to the control module by the securing hooks and arch when the arch is captured by the latch mechanism; and
   a fluid transport tube disposed along the first major surface of the body;
   wherein each of the first and second securing hooks has a hook shape that includes a bearing surface configured to bear against a corresponding one of the two hinge pins when the pressure plate is secured to the control module, each bearing surface facing the first major surface of the body, each bearing surface being flat along the longitudinal axis and parallel along the longitudinal axis with respect to the first major surface to within five degrees,
   wherein the pressure plate and the control module are structured such that relative longitudinal play between the pressure plate and the control module exists over a longitudinal range of motion when the pressure plate is secured to the control module via the securing hooks and the arch; and
   wherein the first and second securing hooks are positioned relative to the body such that, and the hook shape of each of the first and second securing hooks is provided such that, when the pressure plate is secured to the control module, each of the two hinge pins of the control module contacts only the bearing surface of the corresponding securing hook of the pressure plate at a contact point anywhere in a contact range that extends longitudinally in each direction by at least a pre-selected distance about a nominal contact point, such longitudinal displacement of the contact point from the nominal contact point being attributable to the combined variations of: (a) pump separation relative to a pump nominal separation, (b) plate separation relative to a plate nominal separation, and (c) longitudinal play over the longitudinal range of motion.

2. The pressure plate of claim 1, wherein the pre-selected distance is in a range between about 0.70 mm and about 1.00 mm.

3. The pressure plate of claim 1, wherein each bearing surface is flat along a bearing surface length of at least about 1.40 mm.

4. The pressure plate of claim 1, wherein the bearing surface is parallel along the longitudinal axis with respect to the first major surface to within one degree.

5. The pressure plate of claim 1, wherein each of the first and second securing hooks further includes:
   a secondary surface making at least a 45 degree angle with respect to the bearing surface, the secondary surface generally facing the corresponding hinge pin when the pressure plate is secured to the control module; and
   a transition surface between the bearing surface and the secondary surface;
   wherein each of the two hinge pins has a hinge pin radius; and
   wherein the transition surface of each of the first and second securing hooks has a radius not greater than the hinge pin radius but not less than 80% of the hinge pin radius.

6. The pressure plate of claim 5, wherein the secondary surface of each of the first and second securing hooks is substantially perpendicular to the bearing surface.

7. The pressure plate of claim 1, wherein the first securing hook has a first width in the transverse direction and the second securing hook has a second width in the transverse direction different than the first width.

8. A pressure plate configured to couple to a control module of an infusion pump, comprising:
a body having first and second major surfaces, a longitudinal axis and a transverse axis, first and second longitudinal sides, and first and second transverse ends;
first and second pump-securing securing extensions projecting away from the first major surface of the body adjacent the first transverse end, each of the first and second pump-securing securing extensions structured to reversibly and hingedly couple to a corresponding hinge pin of the control module, each pump-securing extension including:
a bearing surface configured to bear against the corresponding hinge pin, the bearing surface facing the first major surface of the body, the bearing surface being flat along the longitudinal axis and parallel along the longitudinal axis with respect to the first major surface to within five degrees;
a secondary surface making at least a 45 degree angle with respect to the bearing surface, the secondary surface generally facing the corresponding hinge pin when the pressure plate is secured to the control module; and
a transition surface between the bearing surface and the secondary surface, the transition surface having a radius not greater than a hinge pin radius of the corresponding hinge pin but not less than 80% of the hinge pin radius; and
an arch extending away from the first major surface of the body adjacent the second transverse end, the arch configured to be captured by a latch of the control module.

9. The pressure plate of claim 8, wherein the transition surface has a radius not less than about 90% of the hinge pin radius.

10. The pressure plate of claim 8, wherein the secondary surface of each of the first and second securing hooks is substantially perpendicular to the bearing surface.

11. The pressure plate of claim 8, wherein the bearing surface is parallel along the longitudinal axis with respect to the first major surface to within one degree.

12. The pressure plate of claim 8, further comprising a fluid transport tube disposed along the first major surface of the body.

13. A pressure plate configured to couple to a control module of an infusion pump, the control module being structured to receive the pressure plate along a mating side of the control module, the mating side having two hinge pins disposed proximal a first end of the mating side, the two hinge pins further being co-linear along a hinge axis, the mating side also having a latch receptacle disposed proximal a second end of the mating side opposite the first end, the control module including a latch mechanism associated with the latch receptacle, the pressure plate comprising:
a body having first and second major surfaces, a longitudinal axis and a transverse axis, first and second longitudinal sides, and first and second transverse ends;
first and second securing hooks extending away from the first major surface of the body proximal the first transverse end, each of the first and second securing hooks structured to reversibly and hingedly couple to a corresponding one of the two hinge pins;
an arch extending away from the first major surface of the body proximal the second transverse end, the arch structured to be received by the latch receptacle of the mating side of the control module as the pressure plate is pivoted about the two hinge pins toward the control module, the arch further being structured to be captured by the latch mechanism of the control module, the pressure plate being secured to the control module by the securing hooks and arch when the arch is captured by the latch mechanism; and
a fluid transport tube disposed along the first major surface of the body;
wherein each of the first and second securing hooks includes a bearing surface configured to bear against a corresponding one of the two hinge pins when the pressure plate is secured to the control module, each bearing surface facing the first major surface of the body, each bearing surface being flat along the longitudinal axis along a bearing surface length of at least 1.40 mm, and each bearing surface being parallel along the longitudinal axis with respect to the first major surface to within five degrees.

14. The pressure plate of claim 13, wherein the bearing surface length is at least about 1.50 mm.

15. The pressure plate of claim 13, wherein each of the first and second securing hooks further includes a secondary surface making at least a 45 degree angle with respect to the bearing surface, the secondary surface generally facing the corresponding hinge pin when the pressure plate is secured to the control module.

16. The pressure plate of claim 15, wherein the secondary surface of each of the first and second securing hooks is substantially perpendicular to the bearing surface.

17. The pressure plate of claim 15, wherein the two hinge pins of the control module to which the pressure plate is configured to couple have a hinge pin radius, and each of the first and second securing hooks of the pressure plate further includes a transition surface between the bearing surface and the secondary surface, the transition surface radiused such that a pin having the hinge pin radius is able to contact both the bearing surface and the secondary surface without contacting the transition surface.

18. The pressure plate of claim 15, wherein the two hinge pins of the control module to which the pressure plate is configured to couple have a hinge pin radius, and each of the first and second securing hooks of the pressure plate further includes a transition surface between the bearing surface and the secondary surface, the transition surface having a radius not greater than the hinge pin radius but not less than about 80% of the hinge pin radius.

19. The pressure plate of claim 13, wherein the first and second securing hooks are positioned relative to the body of the pressure plate and shaped such that when the pressure plate is secured to the control module, each of the two hinge pins of the control module contacts only the bearing surface of the corresponding securing hook of the pressure plate.

20. The pressure plate of claim 13, wherein the fluid transport tube provides a fluid path substantially parallel to the first major surface of the body of the pressure plate, the fluid path extending completely to the first transverse end of the body.

21. An infusion pump system comprising:
a control module configured to pump fluid supplied from a reservoir, the control module including a mating side, the control module having two hinge pins disposed on the mating side, the control module also having a latch mechanism disposed on the mating side, the hinge pins and latch mechanism being spaced apart by a pump nominal separation;

a pressure plate configured to couple to the control module, wherein the control module is structured to receive the pressure plate along the mating side of the control module, the pressure plate including:

a body having first and second major surfaces, a longitudinal axis and a transverse axis, first and second longitudinal sides, and first and second transverse ends;

first and second securing hooks extending away from the first major surface of the body proximal the first transverse end, each of the first and second securing hooks structured to reversibly and hingedly couple to a corresponding one of the two hinge pins;

an arch extending away from the first major surface of the body proximal the second transverse end, the arch structured to be captured by the latch mechanism of the control module, the pressure plate being secured to the control module by the securing hooks and arch when the arch is captured by the latch mechanism; and a fluid transport tube disposed along the first major surface of the body of the pressure plate such that when the pressure plate is secured to the control module, the fluid transport tube is disposed between the pressure plate and the control module adjacent the mating side of the control module;

wherein each of the first and second securing hooks includes a bearing surface configured to bear against a corresponding one of the two hinge pins when the pressure plate is secured to the control module, each bearing surface facing the first major surface of the body, each bearing surface being flat along the longitudinal axis along a bearing surface length of at least 1.40 mm, and each bearing surface being parallel along the longitudinal axis with respect to the first major surface to within five degrees, and wherein the first and second securing hooks are spaced-apart from the arch and shaped such that when the pressure plate is secured to the control module, each of the two hinge pins of the control module contacts only the bearing surface of the corresponding securing hook of the pressure plate.

* * * * *